United States Patent [19]
Perelman et al.

[11] Patent Number: 5,919,140
[45] Date of Patent: Jul. 6, 1999

[54] OPTICAL IMAGING USING TIME GATED SCATTERED LIGHT

[75] Inventors: Lev T. Perelman, Malden; Jun Wu, Cambridge; Yang Wang, Sommervile; Ramachandra Rao Dasari, Lexington; Irving Itzkan, Boston; Michael S. Feld, Newton, all of Mass.

[73] Assignee: Massachusetts Institute of Technology, Cambridge, Mass.

[21] Appl. No.: 08/549,623

[22] Filed: Oct. 27, 1995

Related U.S. Application Data

[63] Continuation-in-part of application No. 08/391,209, Feb. 21, 1995, abandoned.

[51] Int. Cl.⁶ ..................................................... A61B 6/00
[52] U.S. Cl. .............................. 600/476; 600/310; 606/3; 607/88
[58] Field of Search ........................................ 128/664, 665, 128/633, 634; 356/433, 435, 342, 343, 338, 432; 250/330–334, 574, 575, 358.1; 600/473, 476, 310, 342; 606/3; 607/88, 89

[56] References Cited

U.S. PATENT DOCUMENTS

| | | | |
|---|---|---|---|
| 4,515,165 | 5/1985 | Carroll | 128/664 |
| 4,649,275 | 3/1987 | Nelsen et al. | 250/358.1 |
| 4,877,966 | 10/1989 | Tomei et al. | 250/458 |
| 4,973,848 | 11/1990 | Kolobanov et al. | 250/458.1 |
| 5,115,137 | 5/1992 | Andersson-Engels et al. | 250/461.2 |
| 5,148,022 | 9/1992 | Kawaguchi et al. | 250/341 |
| 5,185,521 | 2/1993 | Kvasnik et al. | 250/227.23 |
| 5,227,797 | 7/1993 | Murphy | 342/22 |
| 5,261,410 | 11/1993 | Alfano et al. | 128/664 |
| 5,309,912 | 5/1994 | Knuttel | 128/653.1 |
| 5,323,008 | 6/1994 | Studholme | 250/458.1 |
| 5,349,951 | 9/1994 | Ito et al. | 128/633 |
| 5,371,368 | 12/1994 | Alfano et al. | 250/341.1 |
| 5,421,337 | 6/1995 | Richards-Kortum et al. | 128/665 |
| 5,467,767 | 11/1995 | Alfano | 128/665 |

FOREIGN PATENT DOCUMENTS

| | | |
|---|---|---|
| 0 692 708 | 1/1996 | European Pat. Off. . |
| 95/02987 | 2/1995 | WIPO . |

OTHER PUBLICATIONS

Yamada et al., "Simulation of Time–Resolved Optical Computer Tomography Imaging", *2417 Optical Eng.* vol. 32:3 (Mar. 1993) pp. 634–641.

Mitic et al., "Time–Gated Transillumination of Biological Tissues and Tissuelike Phantoms", *Applied Optics* vol. 33:28 (Oct. 1, 1994) pp. 6699–6710.

de Haller et al., "Resolution of Time–Resolved Breast Transillumination; In vitro Measurements compared With Theoretical Predictions", *Optical Eng.* vol. 34:7 (1995) Jul. pp. 2084–2091.

Wu et al., "Time–Resolved Multichannel Imaging of Fluorescent Objects Embedded In Turbid Media", *Optics Letters* vol. 20:5 (Mar. 1, 1995) pp. 489–491.

Wu et al., "Three–Dimensional Imaging Of Objects Embedded In Turbid Media With Fluorescence and Raman Spectroscope", *Applied Optics* vol. 34:18 (Jun. 20, 1995) pp. 3425–3430.

Perelman, et al., "Time–Dependent Photon Migration Using path Integrals", *Physical Review E* vol. 51:6 (Jun. 1995) pp. 6134–6141.

(List continued on next page.)

*Primary Examiner*—Marvin M. Lateef
*Assistant Examiner*—Shawna J Shaw
*Attorney, Agent, or Firm*—Hamilton, Brook, Smith & Reynolds, PC

[57] ABSTRACT

The present invention relates to the use of time gated scattered light, for determining the location and composition of material within various organs of the human body. The systems and methods of the present invention provide for medical imaging in three dimensions of internal body structures for diagnostic purposes.

28 Claims, 9 Drawing Sheets

OTHER PUBLICATIONS

Alfano et al., "Time–Resolved Ballistic, Snake and Diffusive Imaging", *OSA Proceedings*, Chapter 3, *"Advances In Optical Imaging and Photon Migration"* (Mar. 21–23, 1994) pp. 122–173.

Yodh et al., "Spectroscopy and Imaging With Diffusing Light", *Physics Today* (Mar. 1995) pp. 34–40.

Perelman et al., "Photon Migration In Turbid media using path integrals", *Physical Review Letters* vol. 72:9 (Feb. 28, 1994) pp. 1341–1344.

Wang et al., "Ballistic 2–d Imaging Through Scattering Walls Using an Ultrafast Optical Kerr Gate", *Science* vol. 253 (Aug. 16, 1991) pp. 769–771.

Perelman et al., "Optical Imaging in Turbid Media Using Early Arriving Photons", *SPIE* vol. 2389, pp. 10–15.

OPTICAL IMAGING USING TIME GATED SCATTERED LIGHT

RELATED APPLICATIONS

This is a Continuation-in-Part application of U.S. application Ser. No. 08/391,209, now abandoned which was filed on Feb. 21, 1995 and is incoporated herein by reference in its entirety.

This invention was made with government support under Grant Number NIH-5-P41-RR02594 awarded by the National Institutes of Health. The government has certain rights in the invention.

BACKGROUND OF THE INVENTION

The present invention relates to medical and diagnostic imaging systems and procedures. Clinical procedures currently employ a number of systems for locating, imaging and diagnosing various structures within the human body. These include x-ray computer tomography, ultrasound, and magnetic resonance imaging, among others. These systems are used to detect morphologic abnormalities associated with specific diseases or conditions in various body organs.

In the case of x-ray computer tomography, for example, a number of projection data are taken sequentially at different angles and the data are used to reconstruct an image of the object being scanned in three dimensions. Thus, an x-ray tomography system solves an inverse problem for the x-ray opacity of body tissues using measurements of the amount of radiation absorbed from many beams transmitted at a variety of angles. This procedure is based on a number of assumptions including that the intensity of the x-rays diminishes across the distance traversed at a rate proportional to the intensity of the beam, that the absorption coefficient depends on the type of tissue along the various beam paths and that this non-linear problem can be solved based upon certain approximations including that a linear set of equations is an accurate representation of the problem. Of critical importance to x-ray tomography is that corrections for scattering are relatively simple.

Others have sought to use the "diffusion approximation" to represent the scattering of optical radiation for medical imaging applications. The diffusion approximation involves the detection of incoherent photons and the analysis of the resulting spectrum. The main problem with this approach is poor spatial resolution which limits the usefulness of this method in medical imaging applications. Others have sought to use so-called "ballistic" photons which travel the shortest path through the medium and are, for the purposes of this application, "non-scattered" photons.

A continuing need exists, however, for further improvements in the field of tomographic imaging for medical applications including enhanced resolution, reduced cost and complexity, and improved diagnostic capability.

SUMMARY OF THE INVENTION

The present invention relates to the use of time resolved elastic and inelastically scattered light for locating, imaging and diagnosing structures within organs of the human body. In particular time-resolved photon migration is used for medical imaging, including optical methods for localizing lesions within the body. Since biological tissue is highly scattering, the problem is one of imaging an object embedded in a turbid medium. Most existing techniques use differences in the absorption or elastic scattering properties between the embedded object and its surroundings. In many cases of medical interest, however, the resulting contrast is relatively small, which severely limits the sensitivity and resolution.

Fluorescence spectroscopy studies of human tissue indicate that a variety of lesions show distinct fluorescence spectra compared to those of normal tissue. Thus, intrinsic tissue fluorescence can provide enhanced contrast, as well as diagnostic-histochemical information. In addition, exogenous dyes, many of which are known to fluoresce with high quantum yield, have been shown to exhibit selective uptake in neoplastic lesions. Use of such agents provides fluorescent markers with high quantum yields, and are used to locate embedded lesions in the breast, brain and other organs.

In a preferred embodiment of the present invention time-resolved optical tomography, and fluorescence and Raman spectroscopy, can be used separately or in combination to provide both spatial and chemical information about embedded objects in tissue. By measuring and analyzing the early portion of the fluorescence signal from embedded lesions for example, which rises rapidly and is not sensitive to fluorescence lifetime, precise timing information and hence accurate spatial resolution of embedded lesions can be obtained. The rising edge of the fluorescence signal is generally over a period of 100–200 picoseconds or less. The rising edge of the Raman signal is less than 100 picoseconds. A streak camera can be used as a multichannel time-resolved detector to measure both the rising and decaying periods of the spectrum and to obtain images of embedded fluorescent objects in a single measurement or in a sequence of measurements at one or more angles relative to the tissue.

More specifically, a preferred embodiment collects scattered radiation in the interval between 0 and 1500 picoseconds, and preferably in the range of 0 to 500 picoseconds after irradiation of the tissue, and based upon a comparison of this data with a non-diffusion representation of light which has been scattered by the tissue. This non-diffusion representation emphasizes the "almost straight" trajectories of early arriving photons to provide images of internal bodily structures with improved spatial resolution in the range of 1–3 mm or less. This representation can include a diffusion component for later arriving photons in each collection period which exhibit characteristics more accurately represented by both diffusion and non-diffusion characteristics.

Time resolved Raman scattering of tissue involves the detection of early arriving photons arising from molecular vibration in the objects being measured. The vibrational bands can be assigned to individual molecular groups so that information about molecular content as well as position can be provided.

Optical collectors positioned about the object to be imaged are used to collect fluorescence and/or Raman light scattered by the tissue in response to laser irradiation. The fluorescence and Raman data can be used to locate and image embedded lesions in three dimensions as well as provide information regarding the chemical composition of such lesions. This information can be used to identify such lesions as normal or abnormal, cancerous or precancerous etc. Further details regarding the use of induced fluorescence of tissue to diagnose cancer or precancerous lesions can be found in U.S. Ser. No. 08/219,240 filed on Mar. 29, 1994, now U.S. Pat. No. 5,421,337, the entire contents of which is incorporated herein by reference. The use of laser induced Raman spectroscopy of tissue for diagnosing various diseases and conditions is described in greater detail in U.S.

Ser. No. 08/107,854 filed on Aug. 26, 1993 and having an international filing date of Jan. 17, 1992, and entitled Systems and Methods of Molecular Spectroscopy To Provide For The Diagnosis of Tissue, the entire contents of which is incorporated herein by reference.

Another preferred embodiment utilizes back-scattered fluorescent and/or Raman data to provide measurements of depth and lateral position of lesions in tissue. Fiber optic probes used for back scattering measurements are described in conjunction with the above referenced incorporated applications. The time resolved methods can be used or, alternatively, frequency domain analysis of the acquired spectrum can also be employed. In this embodiment, it is desirable to modulate the laser above 100 MHZ, and preferably between 500 MHZ and 1000 MHZ to provide the temporal resolution for accurately imaging embedded objects. A computer is programmed to transform the data using known transformation techniques and the data can be represented in three dimensions with amplitude plotted as a function of frequency and time.

A preferred method of using the invention to diagnose tissue involves the insertion of a fiber optic probe into a body lumen, collecting data, determining the location of material to be biopsied, and performing a biopsy on the identified material. Additionally, biopsied samples can also be measured and analyzed using the methods described herein. Alternatively, an optical biopsy can be performed in vivo without the need for tissue removal using the methods set forth herein.

The above and other features of the invention including various novel details of construction and combinations of parts will now be more particularly described with reference to the accompanying drawings and pointed out in the claims. It will be understood that the particular system and methods embodying the invention are shown by way of illustration only and not as a limitation of the invention. The principles and features of this invention may be employed in varied and numerous embodiment without departing from the scope of the invention.

DETAILED DESCRIPTION OF THE INVENTION

Figure 1B:
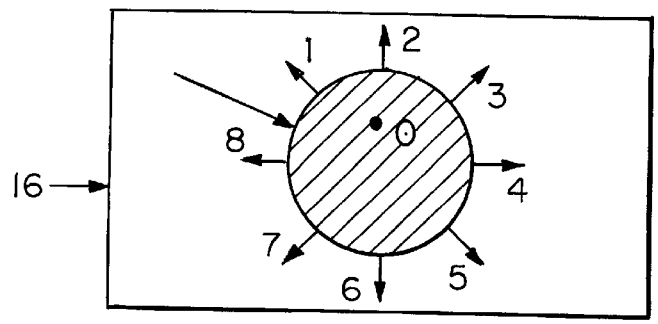
FIG. 1B schematically illustrates a circular multifiber collection geometry.
Figure 1A:
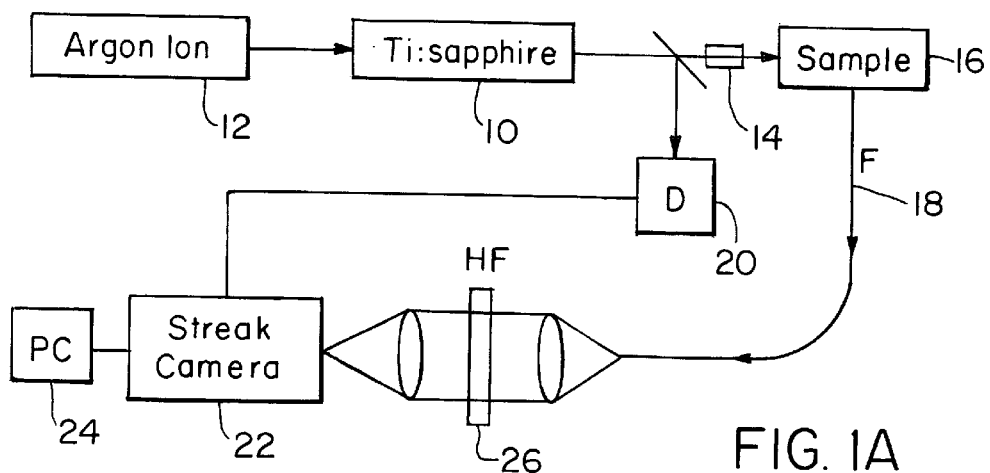
FIG. 1A is a schematic diagram of a tomographic apparatus where O is an embedded fluorescent object; D is a fast photodiode; F are collection fibers; HF is a holographic notch filter.

A schematic diagram of apparatus in accordance with the invention is presented in FIG. 1A. The system can use ~150 fs excitation pulse generated by a Coherent Mira 900 mode-locked Ti:sapphire laser 10 pumped by a Coherent Innova 400 multiline argon ion laser, and a streak camera detection system 22 consisting of a temporal dispenser C1587, synchroscan streak unit M1955 and tuning unit M1954 available from Hamamatsu Photonic Systems Corporation. A photomultiplier detector can also be used. The wavelength in the present embodiment is 750 nm, the repetition rate 76 MHz, and the average power 1.5 W although other wavelengths rates and power levels can be used. A small portion of the excitation light, deflected by a quartz plate to a fast photodiode 20 (D), was used as the optical triggering signal. Eight 100 μm core diameter optical fibers (F) were used to collect the fluorescence light and transmit it to the entrance slit of the streak camera using a fiber optic cable 18. The excitation light can be delivering to the sample along fiber optic cable 14. An endoscopic probe used in conjunction with the invention can incorporate both delivery and fibers. A Kaiser 752 nm holographic notch filter 26 (HF) and two 780 nm long-pass filters were used in front of the streak camera to completely remove the excitation light. The system resolution, 10 ps, was determined by the intrinsic response of the streak camera, and temporal dispersion through the optical fibers, and optical trigger jitter.

Signals can be collected by 8 fibers evenly positioned around the circumference of the medium in the plane containing the fluorescence object (O) as shown in FIG. 1B. Other numbers of fibers and fiber geometries can also be used. Differences in length among the fibers can cause uncertainties in the zeroes of time, but these can be calibrated out. In this arrangement, as shown is FIG. 1B, the fluorescence return signal to be received earliest by the distal end of fiber 2, which is closest to the fluorescent object, and latest by fiber 6, which is furthest away. The proximal ends of these fibers can be arranged in a line and imaged onto the streak camera slit. The streak camera was used as a both time- and spatial-resolved multichannel detector. Signals from different fibers appeared at different vertical locations on the CCD array of the streak camera, and the temporal information was displayed horizontally. The detected data can then be processed by computer 24 to provide the desired time-dependent representation and image of the tissue or features therein and identify the fluorescent or molecular components of interest.

Figure 2:
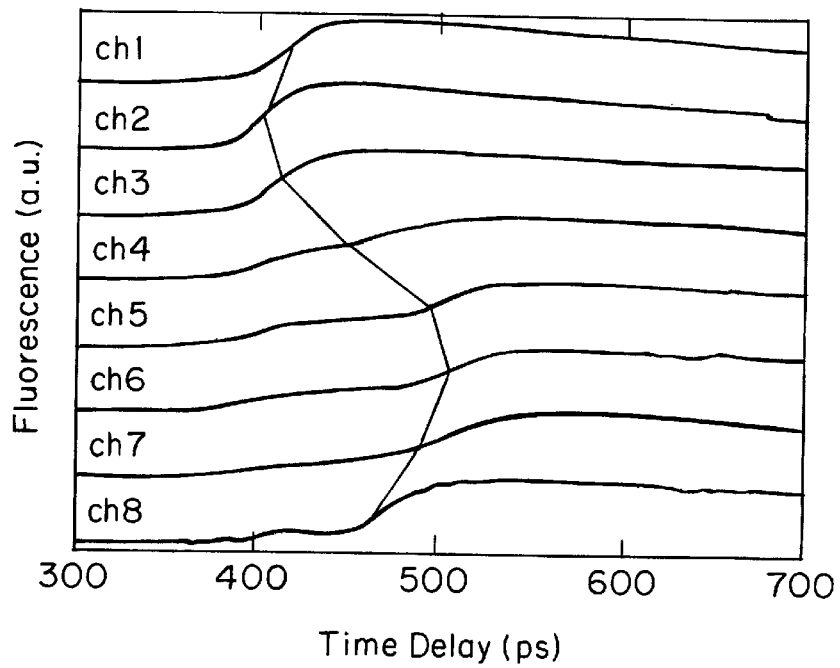
FIG. 2 is an 8-channel time-resolved fluorescence signal observed by the streak camera where the line connects $t_{1/2}$ points of the eight channels.
Figure 3A:
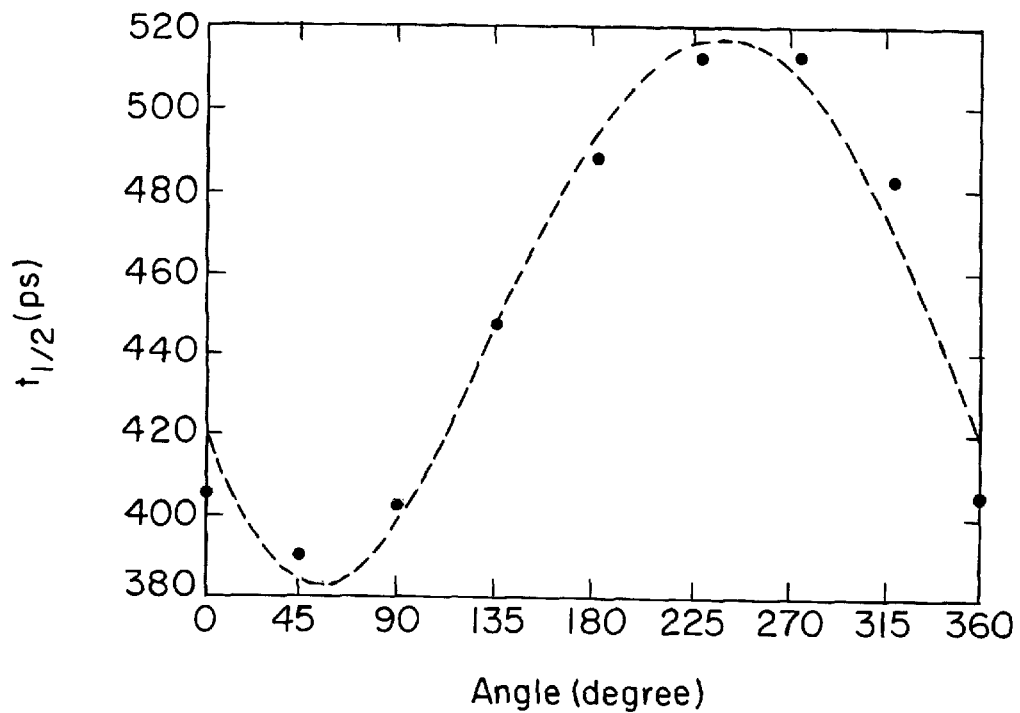
FIG. 3A is a graphical representation where fluorescence signal detected by each individual fiber surrounding the object containing a single embedded object. Fits using a triangulation procedure are plotted as dashed curves.
Figure 3B:
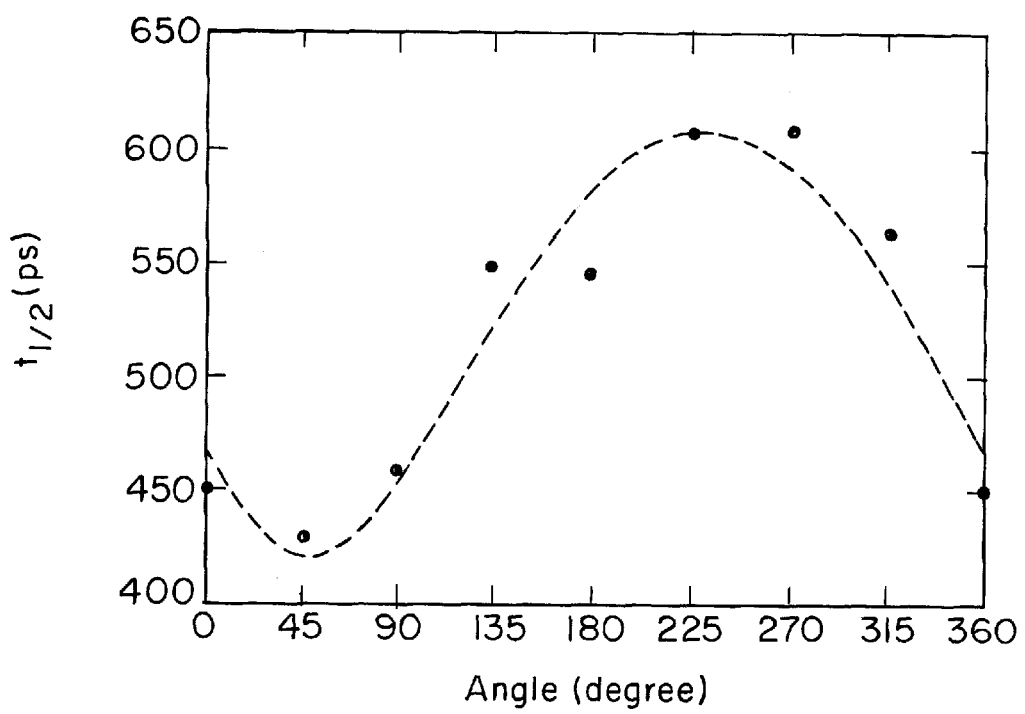
FIG. 3B is graphical representation similar to that of FIG. 3A with a lower mean free path.

A typical 8-channel time-resolved fluorescence signal is shown in FIG. 2. The rising edge of each curve contains timing information which can be used to extract spatial information. The exact timing of these rising edges can be determined in several ways. In the present method the time at which the signal reaches half-maximum of that channel, $t_{1/2}$ was selected at the representative time for each curve. In FIGS. 3A and 3B we plot $t_{1/2}$ for each collection fiber for a single imbedded object for the cases of 1.8 and 0.9 mm scattering mean free path (mfp, $1/\mu_s$), respectively. Note that $\mu_s$ and $\mu_a$ are the scattering and absorption coefficients of the medium. The collection time is 5 minutes in the example, but can be longer or shorter depending on the object to be imaged. The local minimum indicates the position of the object. Similar data were obtained for mfp's between 0.6 and 3.6 mm. (Note that the diameter of the sample is equivalent to 20–120 mfps).

In order to extract the spatial location of the embedded fluorophore, in this procedure it is assumed the time delay for the early photons to be proportional to the distance traveled. In our cylindrical geometry, this can be expressed as $$T_n \propto \sqrt{R^2 + r^2 - 2rR\cos(\theta - \theta_n)},$$

with R the radius of the sample, $\theta_n$ the angular location of the nth channel, and (r, $\theta$) the polar coordinates of the embedded fluorophore. The spatial location of embedded objects can be obtained by fitting the experimental data (e.g. FIGS. 3A and 3B) using Eq. (1). Typical fits are shown as dashed lines in FIGS. 3A and 3B.

Figure 4:
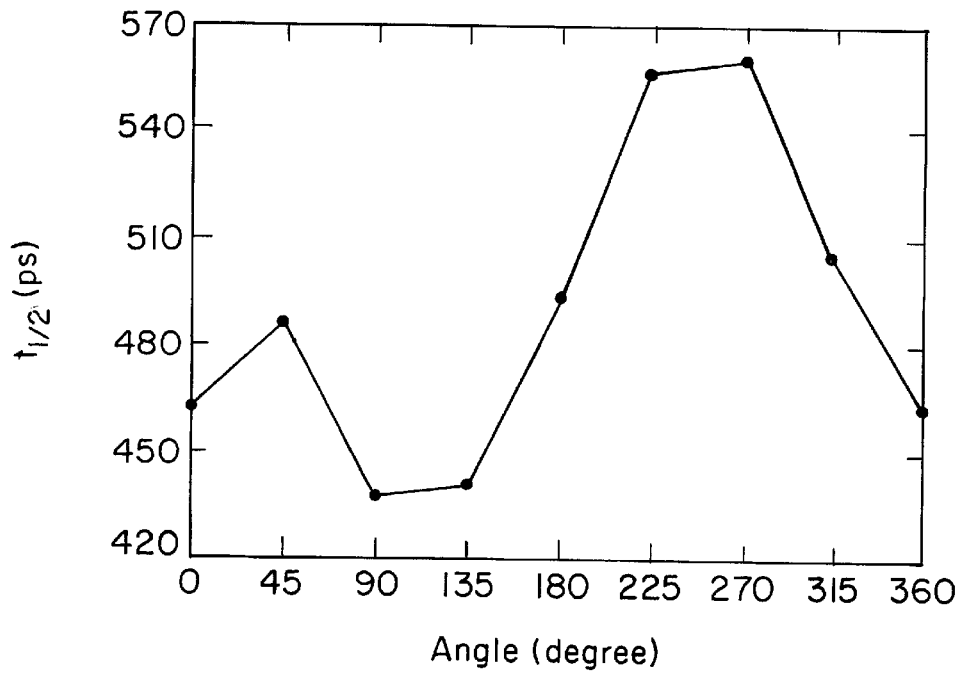
FIG. 4 is a graphical representation where $t_{1/2}$ is the fluorescence signal detected by each individual fiber surrounding a medium containing two embedded objects.

To illustrate the measurement of two embedded objects in which the scattering mfp was 1.8 mm, FIG. 4 plots $t_{1/2}$ for each collection fiber with two objects present. Each local minimum represents a single fluorescing object. Use of more than eight fibers improves the resolution particularly when measuring a number of fluorescing objects. The inverse problem in this case is more complicated and requires an accurate theoretical model of the photon migration process in a turbid medium described in greater detail below.

This geometry is applicable to many human organs, such as brain and breast. Furthermore, this method can be extended to other geometries, as well. Note that with fibers positioned in different planes, objects can be localized in three dimensions. In addition, by observing fluorescence at multiple wavelengths, one can obtain histochemical information.

The streak camera photocathode-window (s-20/UV, spectral response from 200–850 nm) can be more nearly matched to the fluorescent wavelength or wavelengths depending on the fluorescence wavelengths of interest. In addition, the system throughput can be improved by replacing the above fibers with single-mode optical fiber bundles of larger diameter, e.g., 1 mm, without loss of temporal resolution. Improving these factors increases the signal-to-noise ratio by a factor of several hundreds, which permits reduction of the excitation power and/or collection time. The localization accuracy comparable to that of the data presented here can be obtained from a 5 mm diameter fluorescent object containing hematoporphryn derivative (HpD) at clinical concentrations using excitation power of a few tens of mW and less than one minute accumulation time.

In another preferred embodiment the rise-time of fluorescence provides precise timing information, hence accurate spatial resolution, of an embedded object in tissue. Electronic excitation occurs on the optical time scale; and the rise time, which is not affected by fluorescence decay, is on the order of $10^{-13}$ seconds. Raman scattering, another potential source of high contrast, exhibits comparably rapid rise times and can be used for precise timing. Note that these spectroscopic techniques carry the additional potential advantage of providing histochemical information about the object to be imaged. Thus fluorescence emission and Raman scattering are used to obtain time-resolved and three-dimensional spectroscopic information of lesions through overlying tissue.

Figure 5A:
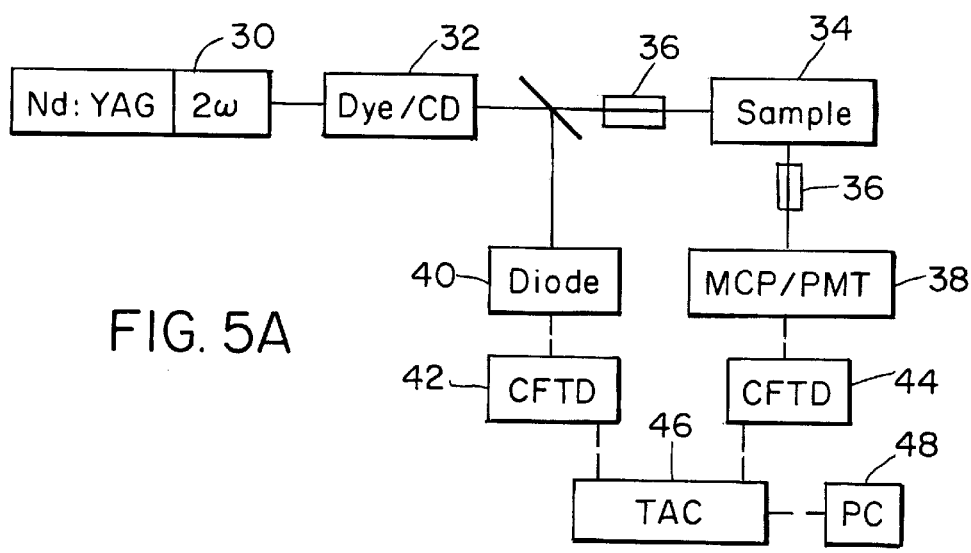
FIG. 5A illustrates a schematic diagram showing instrument components where CD: cavity dumper; MCP/PMT: microchannel plate/photomultiplier tube; CFTD: constant fraction time discriminator; TAC: time-to-amplitude converter; and PC: personal computer. Solid lines represent optic signal paths and dashed electronic signal paths. The insert shows the arrangement of excitation and collection probes, and the sample geometry.
Figure 5B:
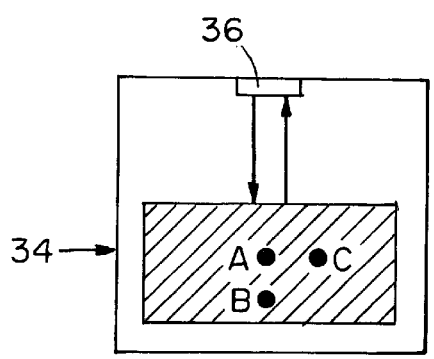
FIG. 5B schematically illustrates an endoscopic backscattering geometry for a fiber optic probe.

A preferred embodiment can use a few-ps pulses for excitation and time-resolved single-photon counting for detection. A wavelength suitable for this application be generated using a Nd:YAG laser 30 to provide radiation at 570 nm, the repetition rate is 1 MHz and the average power is 30 mW. The apparatus is illustrated schematically in FIG. 5A. A 10 nm bandpass filter (centered at 610 nm) and a 600 nm long pass filter in front of the detector completely remove the excitation light. The temporal resolution of the system, about 80 ps, is mainly due to the transit time spread of the PMT. This is adequate to resolve the photon migration signals in our photon samples. Tube 38 is used with a microchannel plate. A constant fraction time discriminator 44 is coupled to tube 38 and the time to amplitude converter 46. An endoscope 36 can be used for delivery and/or collection in backscattering probe procedure for in vivo applications (FIG. 5B). A diode 40 and second CFTD 42 can be used to improve collection prior to analysis on computer 48.

In our singled-ended probing geometry a collection fiber is positioned adjacent to the incident beam on the same surface of the tissue, and the fluorescence material is located at a fixed distance within the tissue. In this geometry the earliest arriving fluorescence photons emitted from the fluorescing material or lesions returns to the collection fiber sooner than those from a second lesion B, located at a greater depth, or a third lesion C, laterally displaced from A. This illustrates the use of a fiberoptic probe in determining the location of the fluorescent object in three dimensions by observing the time-resolved fluorescence signal. Ultrafast time-gating can further improve spatial resolution.

Figure 6A:
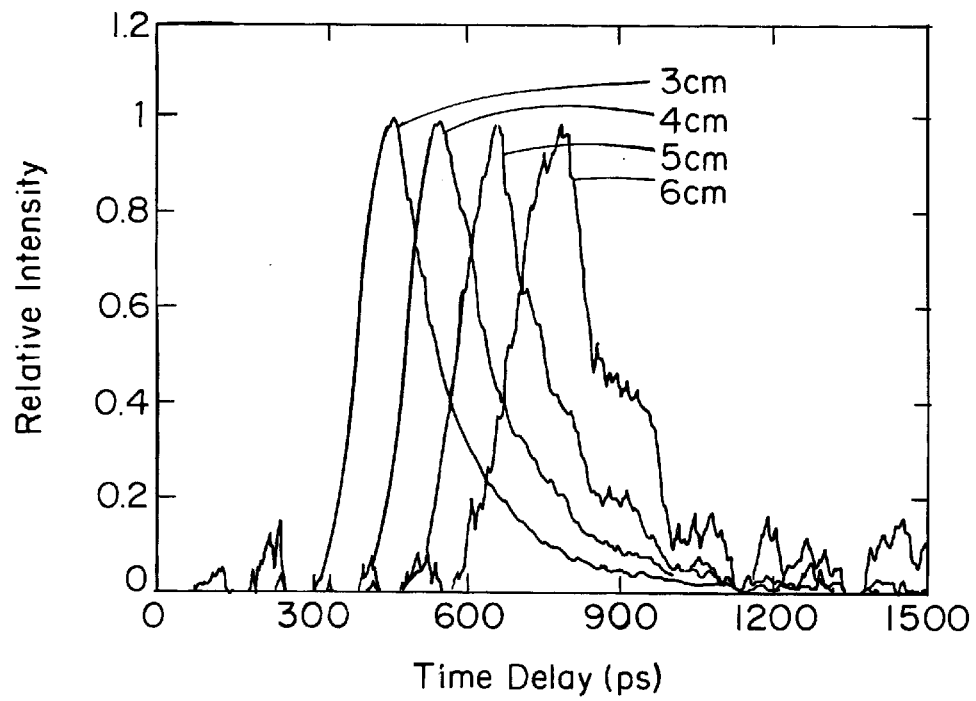
FIG. 6A graphically illustrated a fluorescence emission from rose bengal (RB) dye cell at four different depths.
Figure 6B:
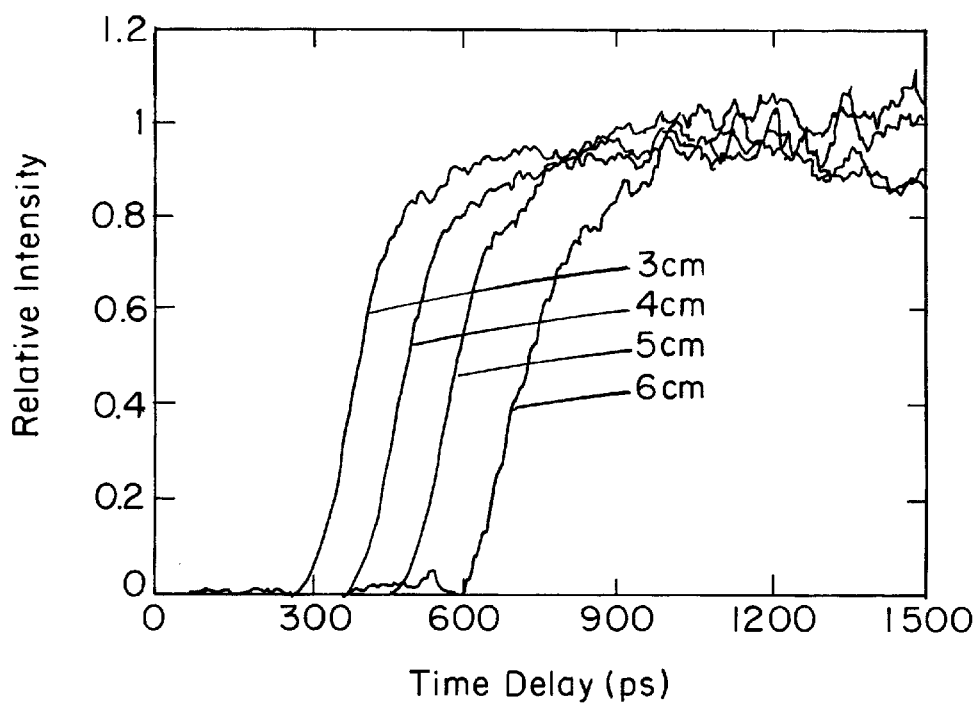
FIG. 6B is a graphical illustration similar to that of FIG. 6A with an rhodamine (R6G) dye cell.

Fluorescence can be used to provide time-of-flight signals for ranging, despite the long fluorescence lifetimes, typically on the order of a few ns, relative to the photon migration time of interest. To illustrate this, we compared the time-resolved signals emitted from dye cells embedded in a polystyrene bead suspension containing either RB (in water lifetime 130 ps) or R6G (lifetime 3.9 ns). The dye cell depth was changed from 3 to 6 cm in 1 cm increments. The scattering mean free path (mfp) was 4 mm. The results are plotted in FIGS. 6A and 6B. In spite of the fact that the fluorescence lifetimes of RB and R6G differ by a factor of 30, the rising edges of these two sets of curves are extremely similar. In fact, they closely represent the rising edge of the photon migration curves.

Figure 7:
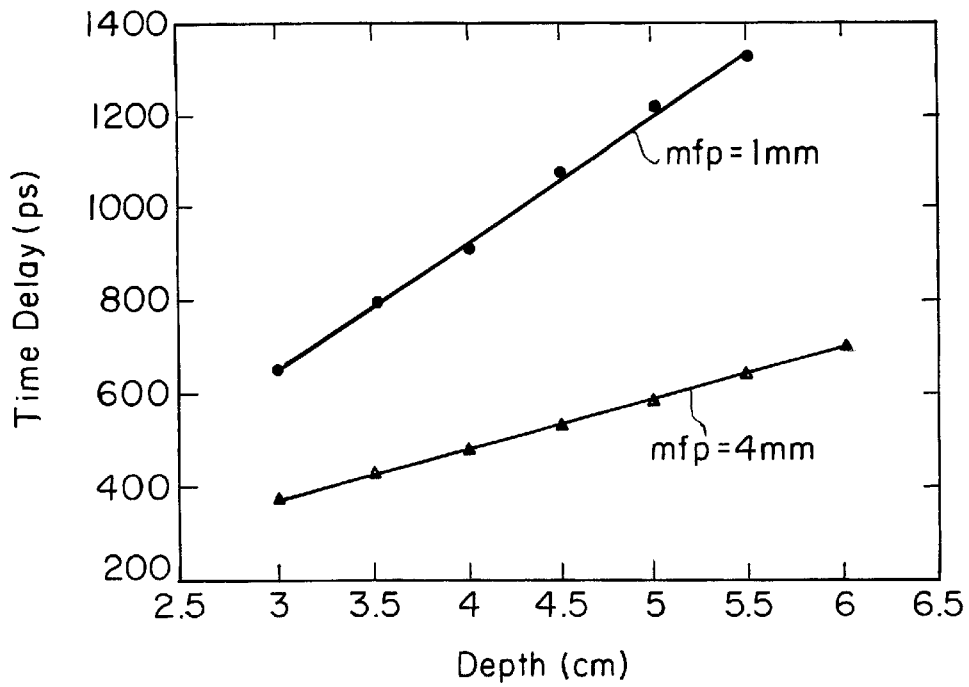
FIG. 7 graphically the depths of a fluorephore vs. $t_{1/2}$ for two different scattering coefficients.

The depths of a fluorescent object can be easily probed in the backscattering geometry by looking at the earliest-arriving fluorescence photons, even under strong scattering conditions. The time-of-flight for these earliest arriving photons is proportional to twice the depth of the fluorescent object. As expected, fluorescence emitted from a deeper object arrives at the detector later. In addition, increased scattering also delays the arrival time, as shown in the plot of depth vs. time, of FIG. 7. The time at which the signal reaches half maximum, $t_{1/2}$ is used as the representative time for each curve. The spatial resolution is determined by both the intrinsic factor, due to the statistics of photon migration, and extrinsic factors such as the sensitivity of the detector and signal-to-noise (S/n) level. With five-minute accumulation time the current set-up can resolve a depth of 1 mm, even at a distance of 100 mfp's.

Figure 8:
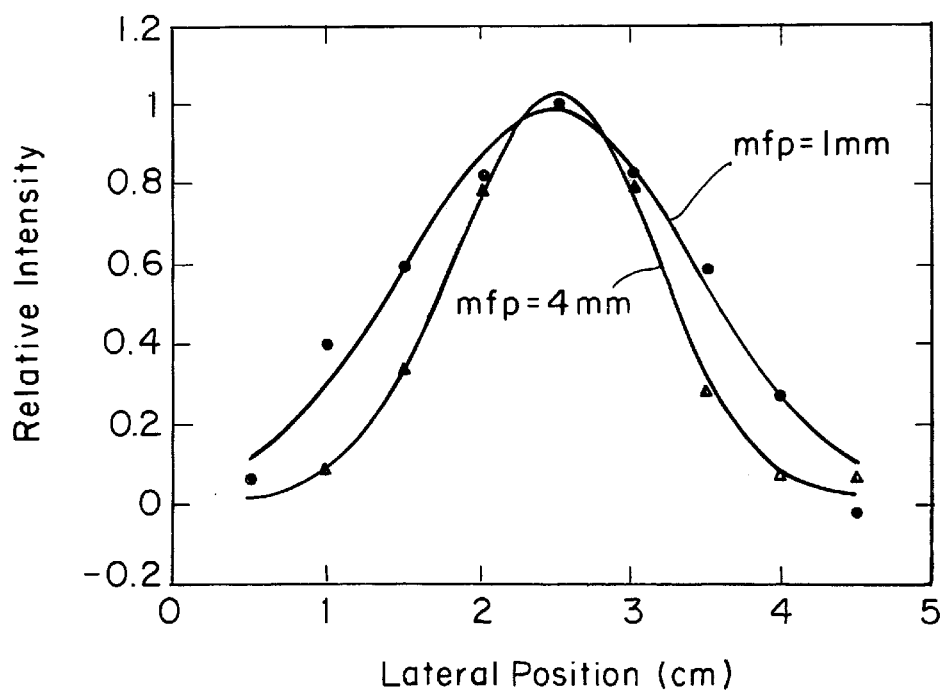
FIG. 8 graphically illustrates lateral location of a fluorophore using ultrafast time-gating for two different scattering coefficients.

To obtain lateral information about an embedded object, we measured the time-resolved fluorescence signals as a function of the lateral position of the dye cell at depth of 5 cm. Based on simple geometrical considerations, we expect lateral resolution to be poorer than depth resolution. However, lateral resolution can be improved by using an ultrafast time window for the earliest arriving photons, which is similar to the typical time-gate transillumination imaging experiments. The optimum time gate was chosen based on considerations of both resolution and S/N ratio. Typically, we used a 24 ps time window. FIG. 8 plots the time gated intensity vs. the lateral displacement of the fluorescence dye cell at 25 and 100 mfp's, respectively. A lateral resolution of 1 cm is obtained with this time window, however, much greater resolutions can be obtained.

Figure 9:
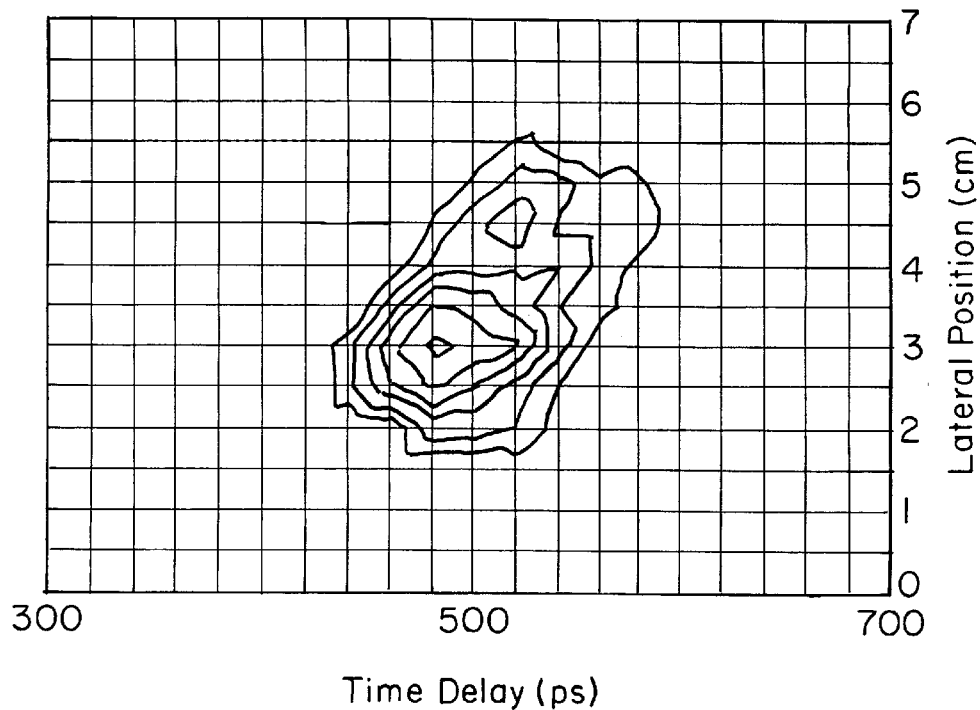
FIG. 9 graphically illustrates the probing two identical fluorophores at different depths.

Measurements were made with two embedded cells containing the same fluorescence dye. The two objects were positioned 1.8 cm apart at depths of 4.5 and 5 cm, respectively. Using lateral displacement and time delay as variables, we can construct a contour map of the time-derivative of the time-resolved intensity (FIG. 9). The time-derivative, a measure of how fast the time-resolved signal evolves, reaches a maximum at approximately $t_{1/2}$, which in turn provides the depth information. Although the signal from the shallower object dominated, the 3-d positions of both objects can be ascertained. This is because we can use different time-gating to provide different depth measurements inside the tissue medium. Note that although the lateral dimension represents the actual image of the object, longitudinally (i.e., temporally) it only provides information about the top surface of the fluorescent material. Also note that the best lateral resolution is obtained at the earliest time gate, i.e., where the contours begin along the time axis.

Figure 10A:
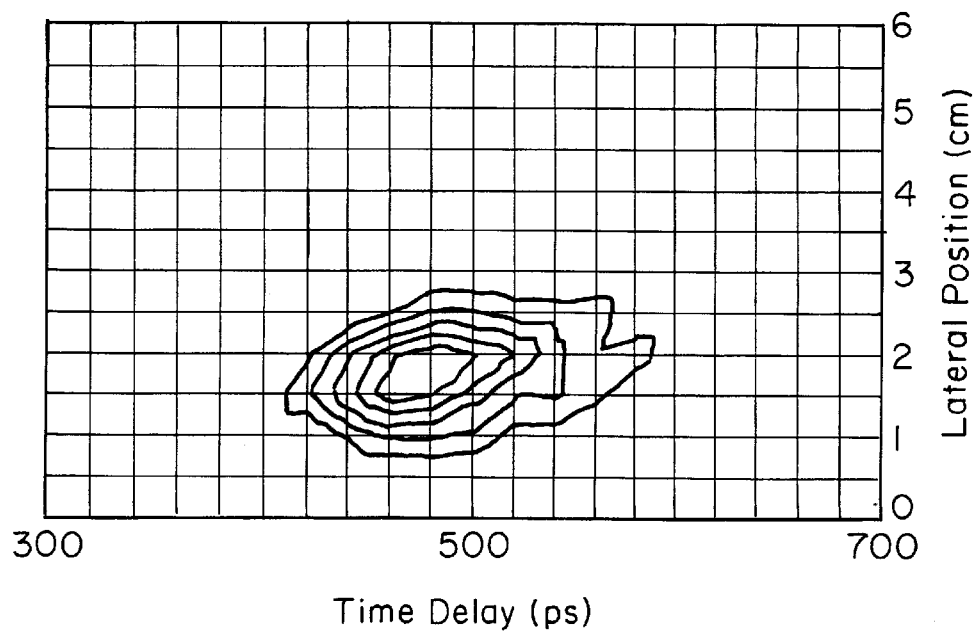
FIGS. 10A and 10B graphically illustrate two different fluorophores detected at 620 nm and 670 nm respectively.
Figure 10B:
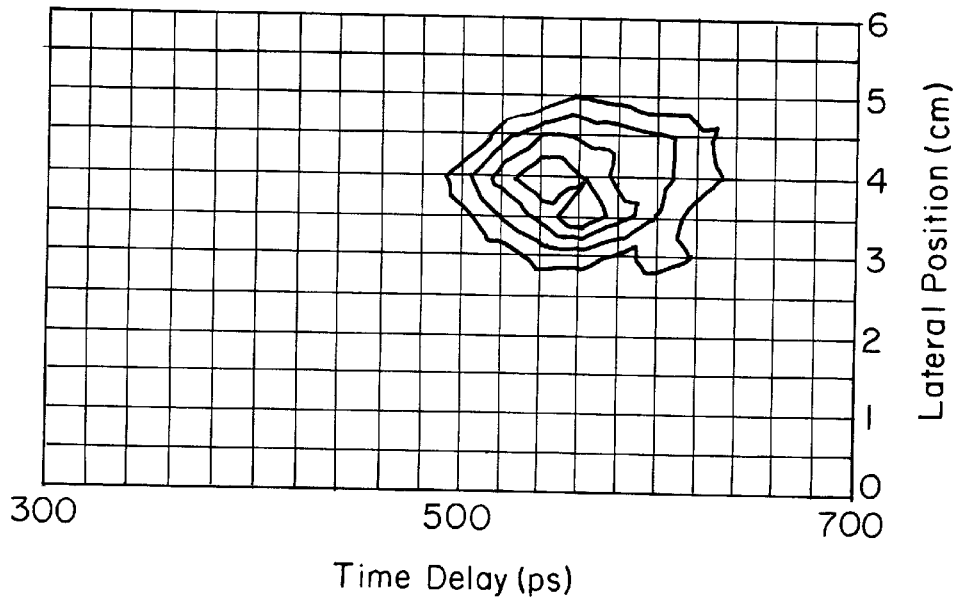

If the two embedded objects have distinct spectroscopic features, imaging capability can be enhanced. This was demonstrated by measuring the fluorescence intensity from two cells (similar geometry as in FIG. 9) containing S640 and HIDCI, respectively, at 620 and 670 nm (FIGS. 10A and 10B respectively) by placing a spectrometer in front of the PMT. Compared to FIG. 9, signal interference between the two objects is reduced, and more importantly, the chemical identities of the objects can be obtained.

Figure 11:
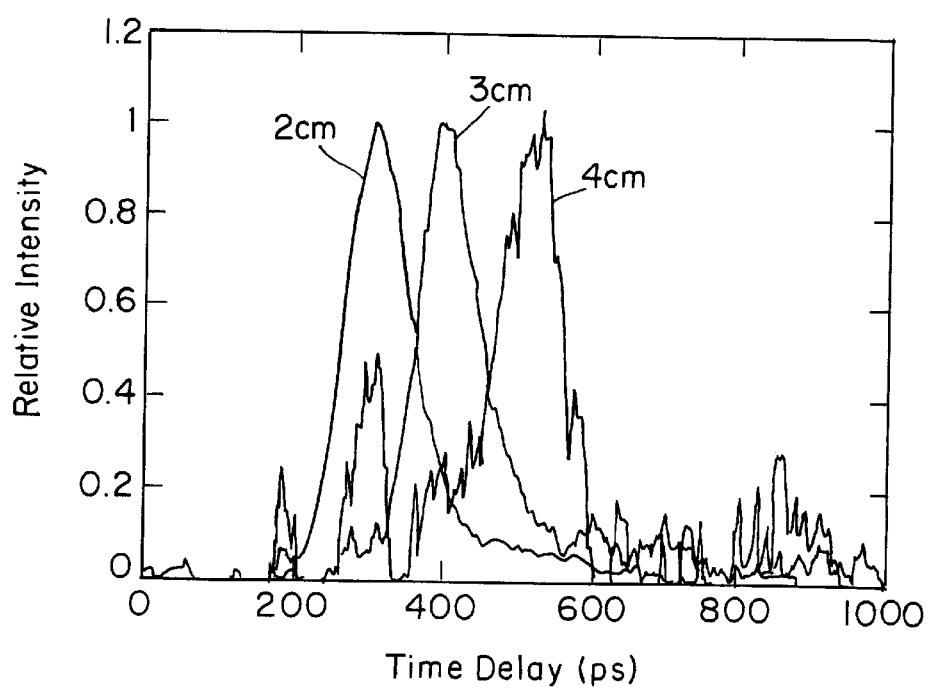
FIG. 11 graphically illustrates results with Raman scattering from β-carotene cell at three depths.

A Raman scattering cell containing β-carotene having a Raman vibration at 1157 cm$^{-1}$ was studied. To establish that the detected signals were from Raman scattering rather than fluorescence from either β-carotene or sample impurities, in a measurement without the scattering medium, the time-resolved Raman scattering was identical in shape to that of the laser light (determined by instrumental resolution), obtained by deflecting part of the laser beam into the fiber probe and removing the filters. This is consistent with the instantaneous nature of Raman scattering. The possibility of laser light leakage was excluded by replacing the Raman cell with a Raleigh scattering cell containing KI powder, which does not have Raman bands above 300 cm$^{-1}$. As a further check, the emission spectrum from the Raman sample was collected using a standard fluorimeter with the same 570 nm excitation. Distinct Raman peaks at 605, 610 and 624 nm, which correspond to the known Raman shifts of 1008, 1157 and 1516 cm$^{-1}$ for β-carotene, were observed with minimum background. FIG. 11 displays the time-resolved Raman signal for cell depths of 2, 3 and 4 cm in a scattering medium with 7 mm mfp.

Thus time-resolved fluorescence and Raman emissions can be used as a probe to provide accurate information about the position of an object such as a lesion embedded in a turbid medium such as tissue. Time resolved fluorescence can be used effectively despite the long fluorescence decay time. The time evolution of the signal is determined by both the time-course of the photons migrating through the scattering media and the decaying fluorescence. These measurements establish that the early portion of the signal rises rapidly and is not sensitive to the relatively long fluorescence lifetime. The early portions of both the fluorescence and Raman signals thus represent the actual time-of-flight of photons traversing the scattering medium. In the case of fluorescence, this is due to the fact that electronic excitation from the ground state to the excited states is extremely rapid, on the order of $10^{-13}$ seconds, so that the rising edge of the fluorescence lifetime curve is effectively a step function. The resulting signal, a convolution of the distribution of the time-of-flight of photons migrating to the detector and the fluorescence decay curve, is mainly determined by that of the time-of-flight curve. In addition, these earliest arriving photons undergo minimal scattering, resulting in high spatial resolution. In other words, by measuring and analyzing the earliest-arriving photons, this serves to minimize the uncertainties due to both diffusive scattering and the finite fluorescence lifetime.

However, unlike many existing trans-illumination methods, a backscattering geometry with single-ended detection is employed. In this configuration, the isotropic fluorescence emission or Raman scattering events serve to reverse the direction of nearly straight photon paths. The earliest signals observed in this case are proportional to twice the distance from the sample surface to the location of the embedded objects, which in our experiments are composed of molecules having unique fluorescence or Raman scattering characteristics. Thus, the arrival time of the earliest photons can provide the depth information of the embedded objects, as well as the usual 2-D localization. In addition, lateral spatial resolution can be optimized by using a short duration time-gate to select the earliest arriving photons. Also, note that in a turbid medium, a backscattering geometry cannot be used with a technique based on elastic scattering or absorption, because photons backscattered by the medium will mask the signals arising from the embedded object.

With the technique presented in this paper, either native tissue chromophores or exogenous dyes can be used to detect embedded lesions. In the former case, both biochemical and spatial information about the lesion are provided simultaneously. The contrast between diseased and normal tissue can be enhanced by utilizing these properties instead of absorption or elastic scattering, and diagnostic information can be obtained. Exogenous dyes, which are known to exhibit fluorescence with high quantum yield, can also be used as a source of contrast. For example, a number of known methods use selective uptake of photosensitizing agents, such as hematoporphyrin derivative, in a neoplastic lesions. Use of such agents provides fluorescent markers with high quantum yields which can serve to locate embedded lesions in the breast, brain or perhaps other organs. The dyes preferably have an excitation wavelength in the range of 600–630 nm and fluorescence in the range of 680–720 nm.

Multichannel detection can be used to extend the capability of the technique presented here in several ways. An optical fiber array can be utilized to obtain 3-D information in a single measurement by displaying physical position along one axis and time along the other. Further more, with the aid of a spectrograph, real-time spectroscopy and optical tomography can be achieved by simultaneously displaying spectral and temporal information.

To understand the differences between prior methods and the present invention it is helpful to consider a system in which photons propagating through a turbid medium from point A to point B can be described using statistical considerations. A photon originating at point A is elastically scattered multiple times, each time being deflected into a particular angle with a well-defined probability, thus forming a trajectory within the medium. Each trajectory has a particular probability. By calculating this probability and then summing over all possible trajectories, one obtains the probability for the photon to travel between two points in the medium.

The probability for a photon to traverse the scattering medium from point A with radius-vector $r_A$ to point B with radius-vector $r_B$ in a time interval T can be written as a path integral:

$$P(r_A, r_B, T) = \int Dr(t) \exp\left\{-\frac{1}{2\mu_s(1-g)} \int_0^T \dot{r}(t)^2 dt\right\} J[\dot{r}(t)], \quad (2)$$

where the function on $$J[\dot{r}(t)] = \int D\Omega(t) \exp\left\{i\mu_s \int_0^T dt \Omega(t)((\dot{r}(t))^2 - 1)\right\}$$

insures that photons propagate at the speed of light in the medium (c=1) at every point along the trajectory, and $$Dr(t) = \prod_{n=1}^{N} dr_n. \quad (3)$$

Integral (2) represents the solution of the equation of radiative transfer for the case in which elastic scattering is described by a Gaussian phase function.

The probability distribution function for the case of isotropic scattering, generally referred to as the diffusive limit, does not follow immediately from Eq. (2), which was derived in the approximation of small angle scattering. However the diffusive limit can be calculated by eliminating the angular dependence of the phase function. Thus, in this case $P(r_A, r_B, T)$ is a path integral over the function $J[r(t)]$:

$$P(r_a, r_b, T) = \int_A^B Dr(t) J[\dot{r}(t)]. \quad (4)$$

By writing the trajectory in the form of a Fourier sine series with a fundamental period of T, an approximate expression for Eq. (3) can be derived:

$$P(R, T) = \begin{cases} 0, & R > T \\ (F(T)\left(1 - \frac{R^2}{T^2}\right)^{3\mu_s T/4}, & R < T \end{cases} \quad (5)$$

where $$F(T) = \frac{2}{T^3 B(3/2, 3\mu_s T/4 + 1)}$$

and $B(\alpha, B)$ is the beta function. This integral takes on different values for T<R and T>R. Note that for T<R the probability (3) is equal to zero, which simply reflects the requirement of causality - - - there is not enough time for a photon initially at A to get to point B. When R<<T, we immediately obtain $$P(R, T) \cong \left(\frac{3\mu_s}{r\pi T}\right)^{3/2} \exp\left(-\frac{3\mu_s R^2}{4T}\right) \quad (6)$$

This formula is a standard result of the time dependent diffusion approximation. In contrast Eq. (4) has the correct properties for times R~T.

$$P(R, T) \cong \left(\frac{3\mu_s}{r\pi T}\right)^{3/2} \exp\left(-\frac{3\mu_s R^2}{4T}\right) \quad (6)$$

This formula is a standard result of the time dependent diffusion approximation. In contrast Eq. (4) has the correct properties for times R~T.

A much more important and interesting case for which the scattering is not isotropic and the phase function is highly peaked in the forward direction. This is the case of relevance to biological tissue. The solution to the transport equation for a sample of infinite extent is given by the integral Eq. (2). Thus:

$$P(r_A, r_B, T) = \quad (7)$$

$$\int_{-\infty}^{+\infty} d\omega \int Dr(t) Q \exp\left\{-\int_0^T \left[\frac{1}{2\mu_s(1-g)}\dot{r}(t)^2 - i\omega(\dot{r}(t)^2 - 1)\right] dt\right\}$$

where Q is a normalization constant. The same approach employed in the diffusive limit can be used to evaluate this integral. Calculations show that the probability depends upon the two factors, one resembling the "diffusion" term which dominates in the long time limit, and the second, which comes into play at short times, and is most important for the early photons that follow short, "almost straight" trajectories. The application of path integral techniques to the problem of light propagation has been set forth by Perelman et al. in "Photon Migration in Turbid Media Using Path Integrals", Physical Review Letters, Vol. 72, No. 9, (1994) the contents of which is incorporated herein by reference. The application of path integral methods for representing light propagation in biological tissue is set forth in Perelman et al., "Time Dependent Photon Migration Using Path Integrals", Physical Review (1995), the contents of which is incorporated herein by reference. In particular, the representation for small angle scattering is of critical importance in accurately imaging embedded lesions using early arriving photons.

To further improve upon the solution to the inverse problem in connection with the use of early arriving scattered photons for medical imaging. One method involves the calculation of the width of the most probable path represented in Eq. (2) to define a "probe." Calculating how many trajectories are eliminated by blocking different parts of this "probe" by an absorbing object inside the tissue, one can determine the change in detected signal as a function of size and position of the object. Thus, the width of the distribution (especially for early times) and amount of signal obtained at the detector becomes important.

For example, using Eq. (2) we calculated a maximum width of the path distribution around a classical path (defined as the width where path density decreases e times from its maximum value) for the 3 cm slab of breast tissue-like medium without absorption ($\mu'_s=10$ cm$^{-1}$, and $\mu=0$). As seen from FIG. 13A, a significant improvement in resolution is obtained by moving the time-gate to shorter times (around 400 ps). The signal level (FIG. 13B) for these times is around 10% of its maximum "diffusive" value, and for a simple shadowgram we can obtain spatial resolution of the order of 3–4 mm, which is 3–4 times better than that obtained using diffusive photons.

Figure 14:
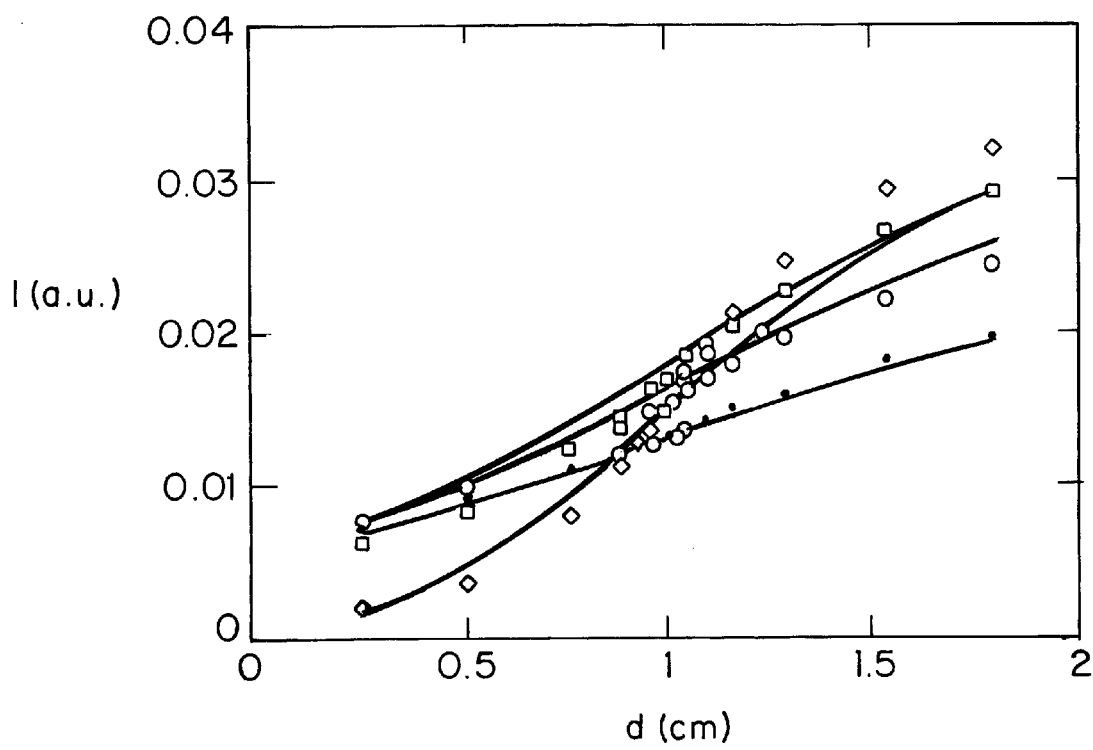
FIG. 14 Detection of the screen edge in the 5.5 cm slab of turbid medium ($\mu'_s=0.45\text{ cm}^{-1}$) with assumption about uniform distribution of the trajectories. Lateral position of the edge is d=1 cm. Theory (solid lines) vs. experiment (dots), where different curves represent time windows at t=310 ps, 450 ps, 500 ps, and 600 ps.

By obtaining the distribution of paths around the classical path in this beam (where one estimates a uniform distribution with a width calculated using the path integral technique, or alternatively, using a Gaussian distribution, which directly comes from Eq. (2)), one can estimate the change in signal because part of the beam is blocked. This provides a relatively simple procedure for creating a data kernel matrix G for early arriving photons. The accuracy of this approximation and the resolution can be calculated from time-resolved transmission through a turbid medium with a screen located in the middle, as a function of source-detector pair position scanner across the medium. FIG. 14 illustrates results of calculations for the direct problem, which was performed using a beam with uniform distribution, and its comparison with a time dependent experiment. Using this simple uniform model for distribution of trajectories inside the beam of early arriving photons, one can locate the edge of the screen in a manner similar to the way it is located in a transparent medium.

Using this method for more complicated geometries and shapes of imbedded objects, a linear system of equations (or G matrix representing the system) defines the temporal signal at the position of the probe as a function of the characteristics and positions of absorbing objects inside the tissue. By determining the generalized inverse $G^{-d}$, one can establish the distribution of the absorbers inside the tissue.

In general terms the data obtained from such a measurement, the data vector f(t) is related to the matrix $G_F$ by a vector of model parameters M: $f(t)=G_F(t)M$. The matrix $G_F(t)$ is provided by the operator $$G_F(r, r_F, t) = \qquad (8)$$

$$\int_v G(r-r_F, t-t'') \exp\left(-\frac{t''-t'}{\tau}\right) G(r_F-r_s, t'-t) Q_s(r_s, t) dr_s dt' dt''$$

where G(r,t) is a photon migration Green's function and $Q_s$ represents the spatial and temporal distribution of the incident laser beam. As this problem is linear, so-called "Maximum Likelihood" methods can be used. Details regarding the use of such methods can be found in *Geophysical Data Analysis: Discrete Inverse Theory* by William Menke, Academic Press C 1989, the contents of which are incorporated herein by reference.

Because the method is based on the concept of the beam of the trajectories, it provides a representation of the photon migration process for early arriving photons and thus provides the data kernel matrix in the way similar to methods used in x-ray tomography. The same procedure can be used for fluorescence measurements of tissue both in vitro and in vivo. Note that the term $G(r-r_F, t-t'')$ in equation (8) represents the incident elastically scattered light, the term $$\exp\left(-\frac{t''-t'}{\tau}\right)$$

represents the fluorescence, where $\tau$ is the fluorescence lifetime and $G(r_F-r_s, t'-t)$ represents the returning scattered light.

The inverse problem can also be addressed for applications in which no linear solution of the inverse problem exists which also provides the resolution and signal strength necessary.

Consider cases where a continuous distribution of absorbing and scattering properties inside the tissue. Note that absorption reduces the probability for realization of the particular trajectory. This can be incorporated into Eq. (2) by multiplying the probability for the specific trajectory by a weight equal to $\exp(-\int \mu_a(r)dr)$, where the integral is calculated along the trajectory. Thus, Eq. (2) can be re-written in the form $$P(r_f, r_s, T) = \int Dr(t) \exp\left\{-\frac{1}{2\mu_s(1-g)}\int_0^T (\dot{r}(t)^2 + V(r(t))dt\right\} J[r(t)] \qquad (9)$$

where the function under the integral in the exponent is the effective Lagrangian in a non-uniformly absorbing medium. It has been generalized by introducing the function $V(r)=2\mu_a(r)\mu_s(1-g)$, associated with absorption. This function has the same properties as a potential, and therefore can be called the effective potential.

Because the most probable path is disturbed by introducing this effective potential, the problem is similar to finding the potential from the form of the particle's trajectory. This problem can be solved by using one of the minimization methods for least square problems described, for example, in more detail in "Generalized non-linear inverse problems solved using least squares criterion," by A. Tarantola and B. Valette in *Rev: Geophys. Space Phys* 20, 219–232 (1982), the contents of which are incorporated herein by reference.

In cases of non-homogeneous scattering coefficient $\mu_s(r)$, the term in front of the action in the exponent will go under the integral. This term, however, does not resemble a potential, but rather a change in particle "effective mass".

Figure 13A:
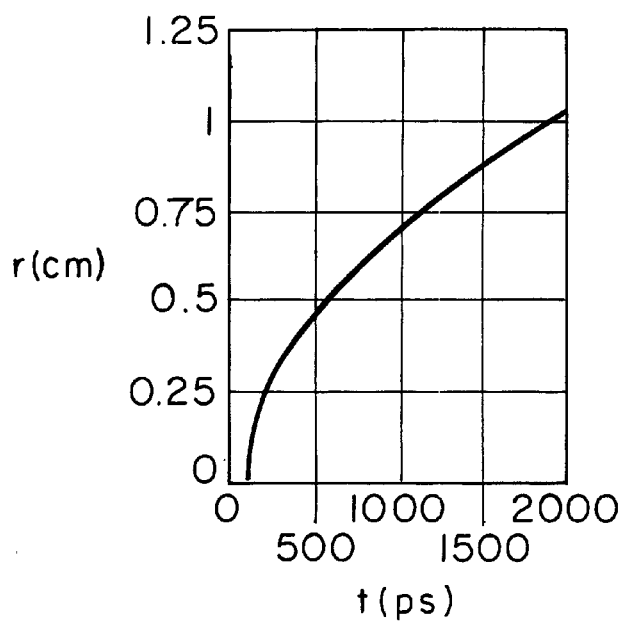
FIGS. 13A and 13B graphically depict the half of the maximum width of path distribution r(a), and relative intensity of emerging light I(b) as a function of time for 3 cm of turbid medium representing breast tissue ($\mu'_s=10\text{-cm}^{-1}$) found from path integral formulation of transport equation.
Figure 13B:
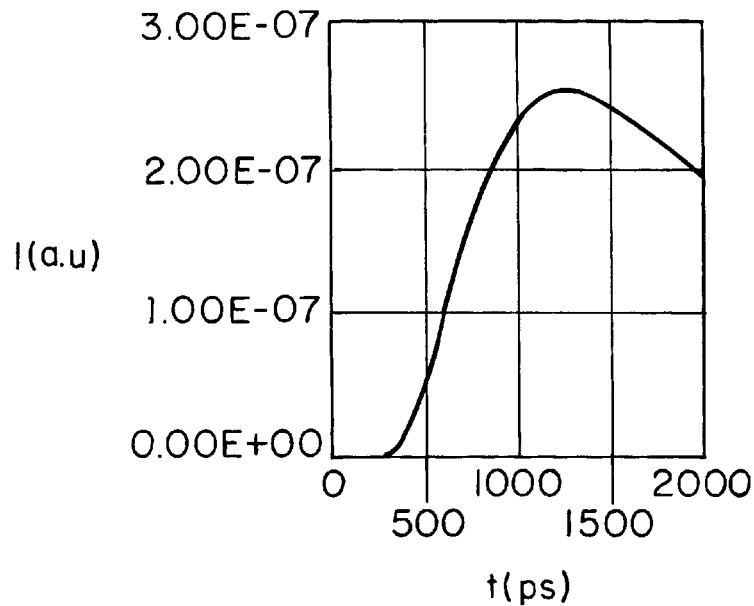

Returning to systems and methods for practicing the invention, as described in connection with FIG. 1, the system can be employed for measurements using ~150 fs excitation pulses generated by a mode-locked Ti:sapphire laser pumped by a multiline argon ion laser, and a streak camera detection system. In another preferred method the incident wavelength was 800 nm, the repetition rate 76 MHz, and the average power 1.5 W. A small portion of the excitation light, deflected by a quartz plate to a fast photodiode, was used as the optical triggering signal. Transmission signals were collected by a 200 μm core diameter optical fiber. The other end of the fiber was imaged onto the streak camera slit. The fiber optic elements can be mounted on a rotating C-arm to position delivery and collection fibers as desired. This actuating mechanism can be operated by suitable motor and computer controlled systems for automatic scanning and collection. The system resolution $$P(r_f, r_s, T) = F(T)\exp \quad (10)$$

$$\left\{ \int_0^T \left[\frac{1}{2\mu(1-g)}\right] \dot{r}_{cl}^2 dt - \frac{3\mu_s(1-g)T^2}{2}\left(\int_0^T (1-\dot{r}_{cl}^2)dt\right)^{-1}\right\},$$

where, F(T) is a normalization function. If we consider a slab of thickness L and introduce a coordinate system in which x and y axes are parallel to the slab's surface and z is normal to this surface, then we can approximately write, $$P(r_f, r_s, W, T) = \quad (11)$$

$$Q\left(\frac{3\mu_s(1-g)}{4\pi}\right)^{3/2} T^{-5/2}(1-(L^2+D^2)/T^2)^{3\mu_s(1-g)T/4} \times$$

$$\exp\left(-\frac{12}{\mu_s(1-g)T^3}\left(L^2 + \left(D - \frac{WT}{2}\right)^2\right) - \frac{W^2}{\mu_s(1-g)T}\right),$$

where D=($D_x$, $D_y$) is a vector that represents displacement of the detected photon from the slab's axes and the vector W describes the angle at which the photon emerges from the slab (See FIGS. 13A and 13B). The components of W=($W_x$, $W_y$) are the angles it makes with the x-z and y-z planes respectively, and Q is a normalization constant.

As can be seen, the probability depends upon two factors, one resembling the "diffusion" term, which dominates in the long time limit, and the second, which comes into play at short times, and is most important for the early photons that follow short, "almost straight" trajectories.

Figure 12:
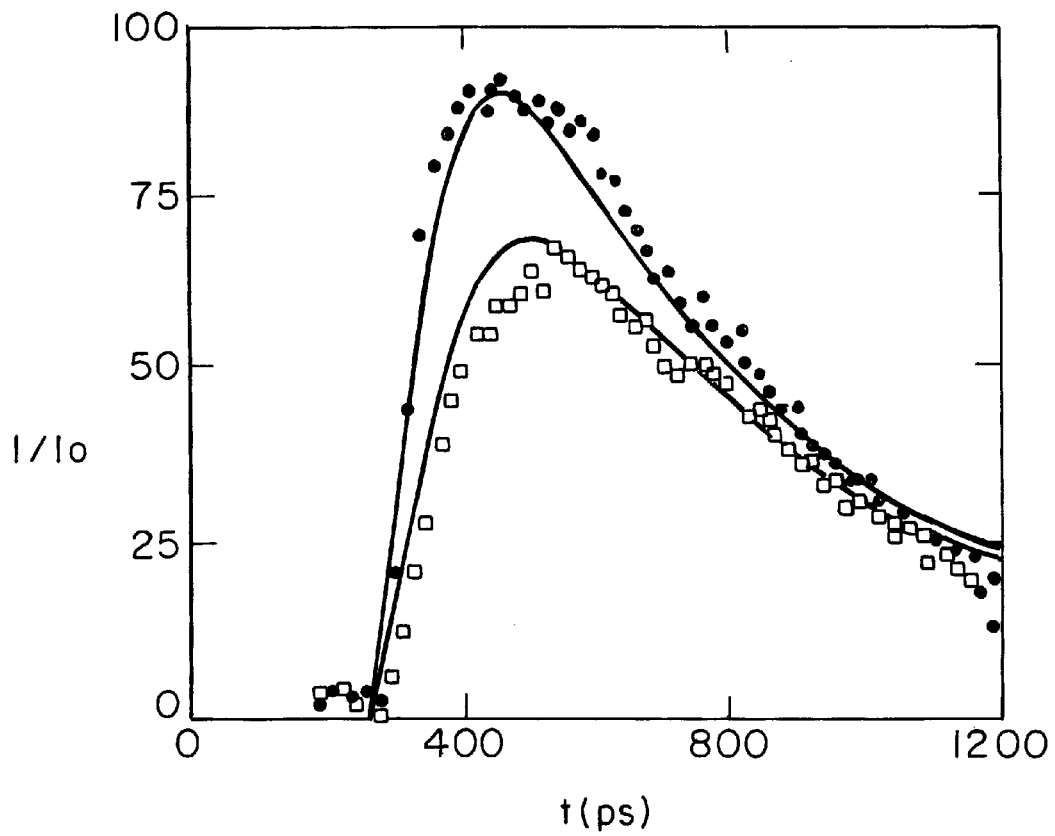
FIG. 12 graphically illustrates time resolved measurements of a turbid medium.

Collected data wre compared with the theoretical representation that follows from Eq. (11). As shown in FIG. 12, results indicate agreement between theory and experiment that can be obtained by varying only one parameter, the scattering coefficient $\mu_s$. This agreement exists not only for the decreasing ("diffusive") part of the curve but also for the initial part of the curve that represents the earliest, highly "non-diffusive" photons. Moreover, FIG. 12 suggests that Eq. (11) has the correct angular dependence.

FIG. 12 shows time-resolved signal measurements for transmission through a slab of turbid media (Intralipid with concentration $C_{Intr}$+10 ml) of thickness L=5.5 cm. The probe was displaced laterally 2 cm from the incident laser beam. Two curves represent two different angles of the probe, θ=40° and θ=−40° measured with respect to the direction of the incident beam. The measured data points are compared with theory (solid lines) with $\mu_s$=3 cm$^{-1}$, g+0.8.

Equivalents

While the invention has been described in connection with specific methods and apparatus, it is to be understood that the description is by way of example and not as a limitation to the scope of the invention as set forth in the claims.

We claim:

1. A method for detecting material within tissue comprising:

irradiating tissue with optical radiation along an optical path, the tissue having material located underneath a surface of the tissue;

collecting scattered optical radiation from the material including a period of rising intensity and a period of decaying intensity;

measuring a rising intensity distribution of the collected optical radiation in a time interval between 0 and 1500 picoseconds after irradiation of the tissue;

comparing the measured rising intensity distribution with a non-diffusion representation of light trajectories in the tissue; and determining the location of the material within the tissue from the comparison of the measured rising intensity distribution and the non-diffusion representation.

2. The method of claim 1 further comprising collecting scattered fluorescent light from the material.

3. The method of claim 1 further comprising irradiating the tissue with substantially monochromatic light from a laser.

4. The method of claim 1 further comprising generating a frequency domain representation of the measured intensity distribution.

5. The method of claim 1 further comprising identifying a fluorphore within the material and determining a distribution of the fluorophore within the material.

6. The method of claim 1 further comprising detecting Raman shifted radiation from the material.

7. The method of claim 1 further comprising comparing the measured intensity distribution collected within the time period between 0 and 500 picoseconds after irradiation of the tissue.

8. A method for detecting material within tissue comprising:

irradiating tissue with radiation from a laser along an optical path;

collecting scattered fluorescent radiation from the material during a rising intensity period with a fiber optic device;

sensing a rising intensity distribution of the collected fluorescent radiation in a time interval between 0 and 500 picoseconds after irradiation of the tissue;

analyzing the sensed rising intensity distribution with a non-diffusion representation; and forming a two dimensional representation of the material within the tissue from the analyzed rising intensity distribution.

9. The method of claim 8 further comprising comparing a rise time of collected scattered fluorescent light with a reference, the reference being formed with a path integral representation of light paths through the tissue.

10. The method of claim 8 further comprising sensing the fluorescent radiation with a streak camera.

11. The method of claim 8 further comprising providing a plurality of optical fibers to collect the scattered fluorescent radiation.

12. The method of claim 8 further comprising providing a fiber optic device to collect the scattered fluorescent radiation.

13. The method of claim 8 further comprising moving a fiber optic device to deliver or collect radiation being directed through the tissue at different angles or positions.

14. The method of claim 8 further comprising sensing the collected light with a charge coupled device.

15. A system for detecting material within tissue comprising:

a laser that irradiates tissue with optical radiation along an optical path;

a fiber optic device that delivers the radiation along the optical path and that collects scattered optical radiation from the material;

a detector that detects a rising intensity distribution of the collected optical radiation in a time interval between 0 and 1500 picoseconds after irradiation of the tissue; and a computer that compares the measured rising intensity distribution with a non-diffusion representation of light trajectories in the tissue stored in a memory of the computer and that forms a two dimensional representation of the material within the tissue.

16. The system of claim 15 further comprising providing a filter to remove a portion of the collected radiation.

17. The system of claim 15 further comprising an actuator that controls movement of the fiber optic device relative to the tissue and the fiber optic device comprises a plurality of optical fibers that collects radiation from the tissue at different angles.

18. The system of claim 15 wherein the detector comprises a streak camera with a charge coupled device.

19. The system of claim 15 further comprising gating means for time gating the collected radiation.

20. A method for detecting material within tissue comprising:

irradiating tissue with radiation from a laser along an optical path;

collecting scattered fluorescent or Raman radiation from the material, the scattered fluorescent or Raman radiation having a rise period and a decay period;

sensing an intensity distribution of the collected fluorescent or Raman radiation in a time interval during the rise period;

analyzing the sensed intensity distribution from the rise period; and forming a representation of the material within the tissue from the analyzed intensity distribution from the rise period.

21. The method of claim 1 further comprising measuring a decaying intensity distribution and forming an image of an imbedded objection in the tissue.

22. A method for detecting material within tissue comprising:

irradiating tissue with optical radiation along an optical path, the tissue having material located underneath a surface of the tissue;

collecting scattered optical radiation from the material;

measuring an intensity distribution of the collected optical radiation in a time interval between 0 and 1500 picoseconds after irradiation of the tissue;

comparing the measured intensity distribution with a path integral representation of light trajectories in the tissue; and determining the location of the material within the tissue from the comparison of the measured intensity distribution and the path integral representation.

23. The method of claim 22 further comprising collecting scattered fluorescent light from the material.

24. The method of claim 22 further comprising irradiating the tissue with substantially monochromatic light from a laser.

25. The method of claim 22 further comprising generating a frequency domain representation of the measured intensity distribution.

26. The method of claim 22 further comprising identifying a fluorphore within the material and determining a distribution of the fluorophore within the material.

27. The method of claim 22 further comprising detecting Raman shifted radiation from the material.

28. The method of claim 22 further comprising comparing the measured intensity distribution collected within the time period between 0 and 500 picoseconds after irradiation of the tissue.

* * * * *